(12) United States Patent
Kashiwada et al.

(10) Patent No.: US 12,031,974 B2
(45) Date of Patent: Jul. 9, 2024

(54) BLOOD CLOTTING TIME MEASUREMENT CARTRIDGE AND BLOOD CLOTTING TIME MEASURING DEVICE

(71) Applicant: APEL CO., LTD., Kawaguchi (JP)

(72) Inventors: Mitsuru Kashiwada, Kawaguchi (JP); Akira Takayama, Kawaguchi (JP); Yasuichi Haga, Goka-machi (JP)

(73) Assignee: APEL CO., LTD., Kawaguchi (JP)

( * ) Notice: Subject to any disclaimer, the term of this patent is extended or adjusted under 35 U.S.C. 154(b) by 739 days.

(21) Appl. No.: 17/260,487

(22) PCT Filed: Sep. 1, 2020

(86) PCT No.: PCT/JP2020/033041
§ 371 (c)(1),
(2) Date: Jan. 14, 2021

(87) PCT Pub. No.: WO2021/049372
PCT Pub. Date: Mar. 18, 2021

(65) Prior Publication Data
US 2022/0011295 A1   Jan. 13, 2022

(30) Foreign Application Priority Data
Sep. 10, 2019 (JP) ................................. 2019-164197

(51) Int. Cl.
*G01N 33/49* (2006.01)
*B01L 3/00* (2006.01)

(52) U.S. Cl.
CPC ...... *G01N 33/4905* (2013.01); *B01L 3/50273* (2013.01); *B01L 3/502715* (2013.01);
(Continued)

(58) Field of Classification Search
CPC ............. G01N 33/4905; B01L 3/50273; B01L 3/502715; B01L 2300/0663; B01L 2300/0816; B01L 2400/049
See application file for complete search history.

(56) References Cited

U.S. PATENT DOCUMENTS

| | | | |
|---|---|---|---|
| 5,372,946 A | * | 12/1994 | Cusak ................ G01N 33/4905 422/534 |
| 5,504,011 A | | 4/1996 | Gavin et al. |

(Continued)

FOREIGN PATENT DOCUMENTS

| | | |
|---|---|---|
| CN | 100371065 C | 2/2008 |
| CN | 102215965 A | 10/2011 |

(Continued)

OTHER PUBLICATIONS

Jul. 5, 2021 Office Action issued in Chinese Patent Application No. 202080003234.5.

(Continued)

*Primary Examiner* — Jill A Warden
*Assistant Examiner* — Alex Ramirez
(74) *Attorney, Agent, or Firm* — Oliff PLC

(57) ABSTRACT

A blood clotting time measurement cartridge that can keep an amount of blood constant while simplifying a configuration and easing a blood injection operation, and a blood clotting time measuring device using the cartridge. The cartridge includes a measurement flow channel wherein blood is housed and transmission of light detects whether there is blood in a predetermined position, an introduction opening on one end side of the channel from which blood is introduced, a communication opening on the other end through which it is possible to cause, by suction or pressurization of air or blood introduced from the introduction opening, the blood in the channel to make a reciprocating motion so as to pass through the predetermined position, a (Continued)

partition wall that partitions a blood injection space connected to the introduction opening, and an absorption member on an outer side of the partition wall that absorbs blood beyond the wall.

4 Claims, 4 Drawing Sheets

(52) U.S. Cl.
CPC ............... *B01L 2300/0663* (2013.01); *B01L 2300/0816* (2013.01); *B01L 2400/049* (2013.01)

(56) References Cited

U.S. PATENT DOCUMENTS

| | | | |
|---|---|---|---|
| 2009/0247902 | A1 | 10/2009 | Reichert et al. |
| 2016/0038939 | A1 | 2/2016 | Min et al. |

FOREIGN PATENT DOCUMENTS

| | | | |
|---|---|---|---|
| CN | 112673260 | A | 4/2021 |
| JP | 855-153133 | U | 11/1980 |
| JP | H03-500573 | A | 2/1991 |
| JP | H11-514087 | A | 11/1999 |
| JP | 2002-214241 | A | 7/2002 |
| JP | 2005-046652 | A | 2/2005 |
| JP | 2006-234590 | A | 9/2006 |
| JP | 2009-279507 | A | 12/2009 |
| JP | 2010-025645 | A | 2/2010 |
| JP | 2010-078608 | A | 4/2010 |
| JP | 2010-243419 | A | 10/2010 |
| JP | 2011-050936 | A | 3/2011 |
| JP | 2012-508879 | A | 4/2012 |
| JP | 2014-044103 | A | 3/2014 |
| JP | 2014-521954 | A | 8/2014 |
| JP | 2014-198324 | A | 10/2014 |
| JP | 2015-510111 | A | 4/2015 |
| JP | 2015-200612 | A | 11/2015 |
| JP | 2015-206608 | A | 11/2015 |
| JP | 2016-520824 | A | 7/2016 |
| JP | 2016-180640 | A | 10/2016 |
| JP | 6415775 | B1 | 10/2018 |
| JP | 2019-124548 | A | 7/2019 |
| JP | 2019-203827 | A | 11/2019 |
| JP | 2019-203872 | A | 11/2019 |
| TW | 201331582 | A | 8/2013 |
| TW | M533212 | U | 12/2016 |
| TW | 201932836 | A | 8/2019 |
| WO | 97/046887 | A1 | 12/1997 |
| WO | 2008/072870 | A1 | 6/2008 |
| WO | 2009/069656 | A1 | 6/2009 |
| WO | 2010/056185 | A1 | 5/2010 |
| WO | 2011/105596 | A1 | 9/2011 |
| WO | 2013/015822 | A1 | 1/2013 |
| WO | 2015/019626 | A1 | 2/2015 |
| WO | 2019/142650 | A1 | 7/2019 |

OTHER PUBLICATIONS

Oct. 12, 2021 Statement of Opinion filed in Chinese Patent Application No. 202080003234.5.
Nov. 30, 2020 Office Action issued in Chinese Patent Application No. 201880028634.4.
Feb. 5, 2021 Statement of Opinion and Amendment submitted in Chinese Patent Application No. 201880028634.4.
Chinese Divisional Application No. 202110117155.3 filed Jan. 28, 2021.
Mar. 26, 2019 Search Report issued in International Patent Application No. PCT/JP2018/048528.
Jul. 10, 2018 Office Action issued in Japanese Patent Application No. 2018-100060.
Aug. 28, 2018 Notice of Allowance issued in Japanese Patent Application No. 2018-100060.
Aug. 2, 2018 Office Action issued in Japanese Patent Application No. 2018-004698.
Oct. 23, 2018 Office Action issued in Japanese Patent Application No. 2018-004698.
Dec. 4, 2018 Notice of Allowance issued in Japanese Patent Application No. 2018-004698.
Sep. 25, 2018 Notice of Allowance issued in Japanese Patent Application No. 2018-140407.
Oct. 7, 2019 Office Action issued in Taiwanese Patent Application No. 108101409.
Feb. 5, 2020 Notice of Allowance issued in Taiwanese Patent Application No. 108101409.
Jun. 3, 2020 Office Action issued in Taiwanese Patent Application No. 108 147 224.
Aug. 10, 2020 Notice of Allowance issued in Taiwanese Patent Application No. 108 147 224.
Oct. 27, 2020 International Search Report issued in International Patent Application No. PCT/JP2020/033041.
Nov. 26, 2019 Office Action issued in Japanese Patent Application No. 2019-164197.
Jan. 22, 2020 Written Amendment submitted in Japanese Patent Application No. 2019-164197.
Mar. 10, 2020 Office Action issued in Japanese Patent Application No. 2019-164197.
Apr. 2, 2020 Written Amendment submitted in Japanese Patent Application No. 2019-164197.
Jun. 30, 2020 Office Action issued in Japanese Patent Application No. 2019-164197.
Jul. 15, 2020 Written Amendment submitted in Japanese Patent Application No. 2019-164197.
Aug. 18, 2020 Notice of Allowance issued in Japanese Patent Application No. 2019-164197.
Dec. 2, 2020 Notice of Allowance issued in Taiwanese Patent Application No. 109130675.
U.S. Appl. No. 16/649,000, filed Mar. 19, 2020.
Jan. 10, 2022 Office Action issued in Chinese Patent Application No. 202110117155.3.
Jan. 26, 2022 Notice of Allowance issued in Chinese Patent Application No. 202080003234.5.
Oct. 9, 2021 Office Action issued in Chinese Patent Application No. 202110117155.3.
Kashiwada, Minoru et al; JP 2015-206608 A; English Machine Translation of Description, obtained from espacenet.com, Jun. 10, 2022; p. 1-26. (Year: 2022).
Yonetani, Akira et al; JP 2011-050936 A; English Machine Translation of Description, obtained on Jun. 10, 2022; p. 1-29. (Year: 2022).
Jun. 15, 2022 Office Action issued in U.S. Appl. No. 16/649,000.

* cited by examiner

BLOOD CLOTTING TIME MEASUREMENT CARTRIDGE AND BLOOD CLOTTING TIME MEASURING DEVICE

TECHNICAL FIELD

The present invention relates to a blood clotting time measurement cartridge used in measurement of time until blood is clotted, and a blood clotting time measuring device that uses this blood clotting time measurement cartridge.

BACKGROUND ART

In a case where extracorporeal circulation such as dialysis or an artificial heart-lung machine used in a surgery of a circulatory system is performed, or a case where treatment of a cardiac catheter is performed, anticoagulant such as heparin is used to prevent clotting of blood. It is important to use an appropriate amount of such anticoagulant since there is a case where an extracorporeal circulation path is occluded when a dosage amount thereof is not enough, and stopping bleeding becomes difficult when a dosage amount thereof is too much. Conventionally, for a determination of a dosage amount or time of dosing of anticoagulant, a method of accelerating clotting of blood by mixing a clotting accelerator into the blood, and of measuring time at which it is determined that a predetermined percentage of the blood is clotted (clotting time of blood) has been used, and various technologies for that have been proposed.

For example, in Patent Literature 1, a technology which includes a measurement cartridge in which a spherical object is arranged in a measurement flow channel, and a measuring device capable of oscillating the set measurement cartridge, and in which the spherical object is made to make a reciprocating motion in the measurement flow channel along with blood in association with oscillation of the cartridge, a clotting accelerator previously applied on the measurement flow channel is dissolved and clotting is accelerated thereby, and clotting time of the blood is measured from a change in time that is necessary for the reciprocating motion of the blood and that is measured at the time is disclosed.

Also, in Patent Literature 2, a cartridge including an opening part in which a space for injecting blood with a dispensing burette or the like is partitioned, a measurement flow channel one end of which is connected to this space to allow introduction of blood and which has a communication opening at the other end, and a diaphragm that pressurizes or depressurizes an air chamber by changing a volume of the air chamber connected to the communication opening is disclosed. Even in such a cartridge, it is possible to measure clotting time while dissolving a previously-applied clotting accelerator into blood and accelerating clotting since it is possible to cause blood in a measurement flow channel to make a reciprocating motion by pressing a diaphragm or releasing the pressing.

CITATION LIST

Patent Literature

Patent Literature 1: Japanese Patent Application Laid-Open No. 2015-200612
Patent Literature 2: Japanese Patent No. 6415775

SUMMARY OF INVENTION

Technical Problem

Incidentally, when an amount of introduced blood varies in such a cartridge, a ratio of a clotting accelerator previously applied to the cartridge to the introduced blood changes. Thus, measurement of clotting time may be affected. Thus, in Patent Literature 1, a piston to draw blood into a measurement flow channel is provided, and an amount of blood introduced into the measurement flow channel is made constant by precise movement of this piston. However, the provision of the piston increases a cost and complicates the configuration. On the one hand, although the cartridge of Patent Literature 2 has a simple configuration, when injecting blood with a dispensing burette or the like, it is necessary to carefully perform an operation in such a manner that an injection amount becomes constant. On the other hand, when blood is injected in such a manner as to overflow from an opening part and an inner side of the opening part is filled with the blood, it is possible to introduce a constant amount of blood into a measurement flow channel without performing an operation that carefully. However, depending on viscosity of blood or the like, there is a case where a height of blood rising from the opening part due to surface tension varies and an amount of blood introduced into the measurement flow channel fluctuates accordingly.

In view of these points, the present invention is to provide a blood clotting time measurement cartridge with which it is possible to keep an amount of blood introduced into the cartridge constant while realizing simplification of a configuration and ease of a blood injection operation and to accurately measure clotting time of the blood accordingly, and a blood clotting time measuring device using this blood clotting time measurement cartridge.

Solution to Problem

The present invention is a blood clotting time measurement cartridge including: a measurement flow channel in which blood is housed and it is detected whether there is the blood in a predetermined position by transmission of light; an introduction opening which is provided on one end side of the measurement flow channel and from which the blood is introduced into the measurement flow channel; a communication opening which is provided on the other end side of the measurement flow channel and through which it is possible to cause, by suction or pressurization of the air in the measurement flow channel or the blood introduced from the introduction opening into the measurement flow channel, the blood in the measurement flow channel to make a reciprocating motion in such a manner as to pass through the predetermined position; a partition wall to partition a blood injection space connected to the introduction opening; and an absorption member that is provided on an outer side of the partition wall and that absorbs blood that is beyond the partition wall.

In such a blood clotting time measurement cartridge, it is preferable that an upper end part of the absorption member is placed as high as or higher than an upper end part of the partition wall.

Also, it is preferable that the absorption member surrounds a whole circumference of the partition wall.

The present invention is also a blood clotting time measuring device to which such a blood clotting time measurement cartridge can be attached and which includes a detection means to detect, with light, whether there is blood in the predetermined position.

Advantageous Effects of Invention

In a blood clotting time measurement cartridge of the present invention, an introduction opening from which blood is introduced into a measurement flow channel is connected to a blood injection space, and an absorption member to absorb blood that is beyond a partition wall that partitions this blood injection space is provided on an outer side of the partition wall. Then, when blood is injected in such a manner as to overflow from the partition wall, the absorption member can absorb the blood that is beyond the partition wall and that includes blood that accumulates in such a manner as to rise from the partition wall due to surface tension. That is, it is not necessary to provide a piston or the like that has been used conventionally, and it is not necessary to carefully perform an operation in such a manner that an amount of blood becomes constant during injection thereof with a dispensing burette or the like. Thus, it is possible to keep an amount of blood introduced into the cartridge constant while realizing simplification of a configuration and ease of a blood injection operation, whereby it is possible to accurately measure clotting time of the blood.

DESCRIPTION OF EMBODIMENTS

In the following, an embodiment of a blood clotting time measurement cartridge (hereinafter, referred to as cartridge) according to the present invention will be described with reference to the attached drawings.

A cartridge of the present embodiment includes a base 1 that is flat as a whole, and a sheet-like blocking plate 2 fixed to the base 1 on a bottom surface side of the base 1.

The base 1 is formed of a colorless transparent synthetic resin. Note that there is no limitation to synthetic resin, and glass or the like may be used. Also, there is no limitation to colorless transparency, and at least a detection area (described later) may have colored transparency with which light is transmitted. Also, what is other than the detection area does not need to be transparent. Also, although being formed of a colorless transparent synthetic resin (thin sheet), similarly to the base 1, the blocking plate 2 can be formed of various materials in various colors as long as a function of the present invention is satisfied. Also, connection between the base 1 and the blocking plate 2 may be adhered by something adhesive, or may be welded, for example, with an ultrasonic wave.

Figure 3:
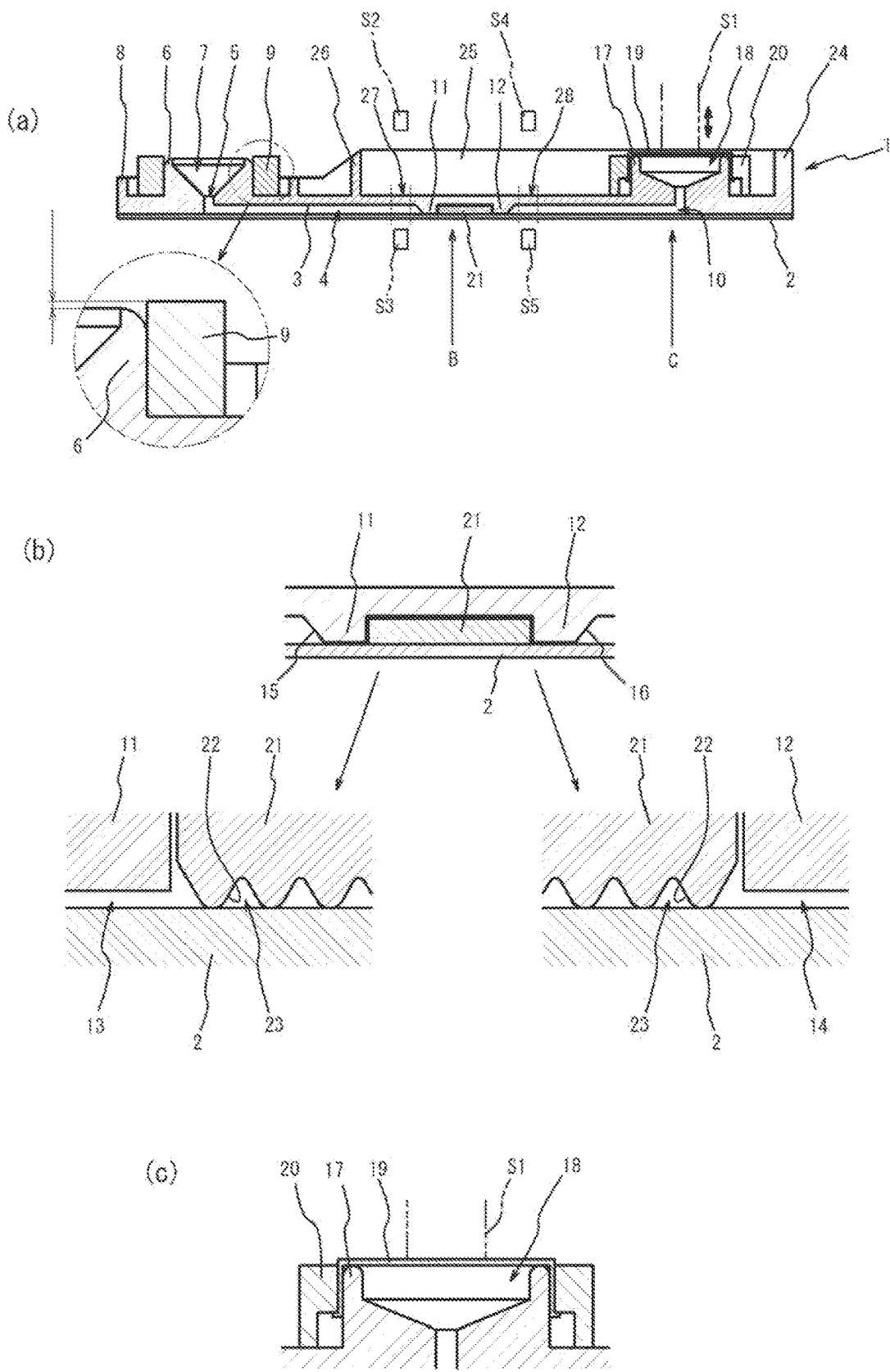
FIG. 3 is a view related to the blood clotting time measurement cartridge illustrated in FIG. 1, FIG. 3(a) being a cross-sectional view taken along an A-A line illustrated in FIG. 2(a), FIG. 3(b) being a partially-enlarged cross-sectional view of a B part illustrated in FIG. 3(a), and FIG. 3(c) being a partially-enlarged cross-sectional view of a C part illustrated in FIG. 3(a).

As illustrated in FIG. 3, a groove part 3 extended long with respect to a cross-sectional area is provided in a bottom surface of the base 1, and a measurement flow channel 4 that houses blood in a manner described later is formed between the groove part 3 and the blocking plate 2.

Then, an introduction opening 5 from which blood can be introduced into the measurement flow channel 4 is provided on one end side of the measurement flow channel 4. Here, a partition wall 6 having a columnar outer peripheral surface and a conical inner peripheral surface is provided on a surface of the base 1, and the introduction opening 5 is connected to a space partitioned inside the partition wall 6 (blood injection space 7). Also, a blood receiving unit 8 having an annular shape is provided on an outer side in a radial direction of the partition wall 6 on the surface of the base 1.

Figure 2:
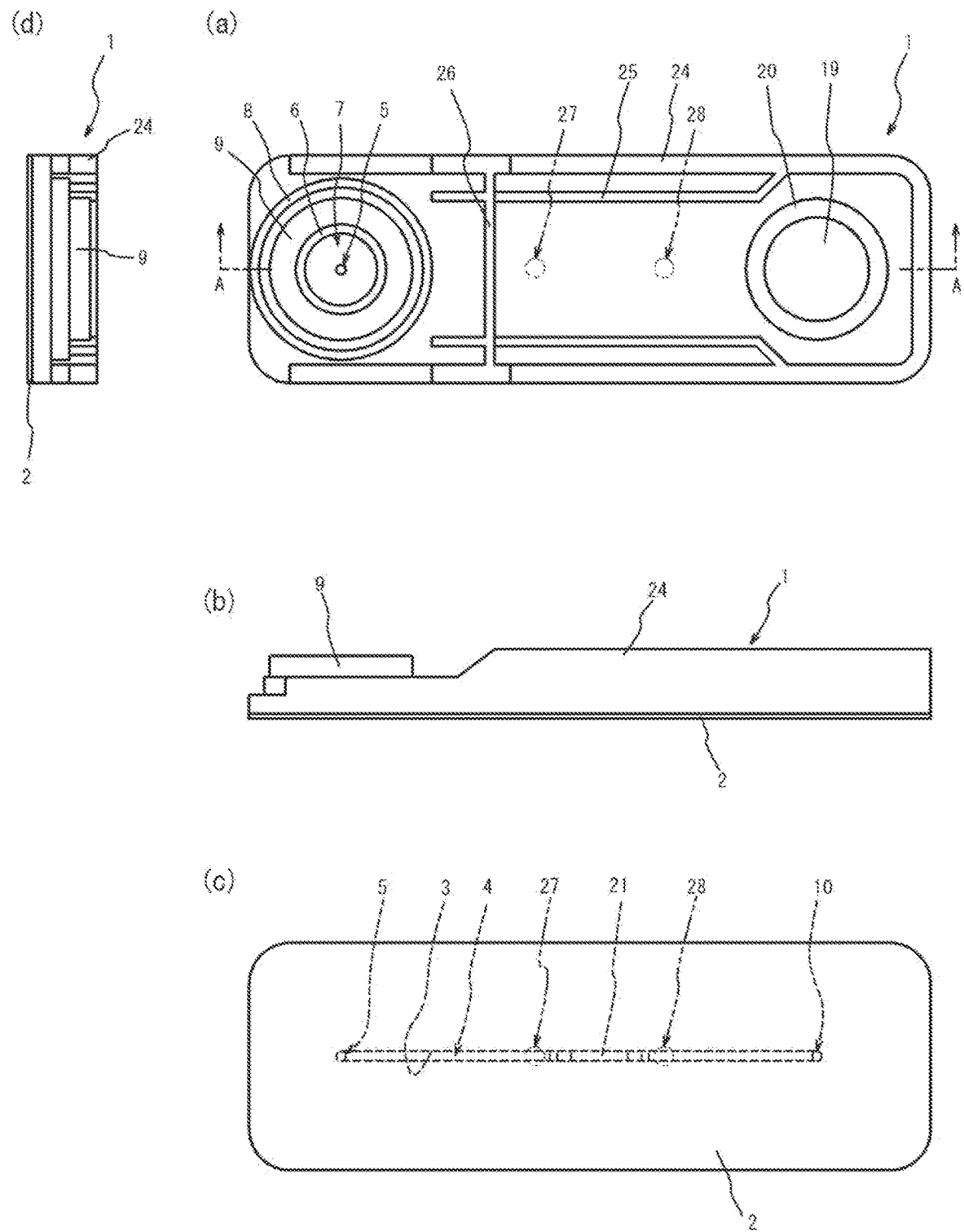
FIG. 2 is a view related to the blood clotting time measurement cartridge illustrated in FIG. 1, FIG. 2(a) being a plan view, FIG. 2(b) being a front view, FIG. 2(c) being a bottom view, and FIG. 2(d) being a right side view.

An absorption member 9 capable of absorbing blood is provided on the outer side in the radial direction of the partition wall 6. The absorption member 9 is formed of a material having an excellent liquid absorption property (for example, foam material such as a sponge, or porous material). Also, as illustrated in FIG. 2, the absorption member 9 of the present embodiment has an annular shape formed in such a manner as to be fitted to the outer peripheral surface of the partition wall 6 (in such a manner that there is no gap with respect to the outer peripheral surface of the partition wall 6). Also, as illustrated in FIG. 3(a), the absorption member 9 is formed to have a thickness with which an upper end part thereof is placed as high as or higher than an upper end part of the partition wall 6 when the absorption member 9 is fitted to the outer peripheral surface of the partition wall 6 in such a manner as to be in contact with a surface of the base 1. Note that the absorption member 9 is preferably fixed to the base 1, for example, with an adhesive tape or an adhesive in such a manner as not to come off from the partition wall 6.

Also, a communication opening 10 is provided on the other end side of the measurement flow channel 4. The communication opening 10 can suction or pressurize air in the measurement flow channel 4 or blood introduced from the introduction opening 5 into the measurement flow channel 4 by changing a pushing amount into a diaphragm (described later).

Then, a pair of protruded parts (one end-side protruded part 11 and other end-side protruded part 12) provided in such a manner as to be protruded to a bottom surface side is provided in a center part of the measurement flow channel 4. With this arrangement, a narrowed part (one end-side narrowed part 13 and other end-side narrowed part 14) in which the measurement flow channel 4 is narrowed down is formed as illustrated in an enlarged view in FIG. 3(b). Also, in the one end-side protruded part 11, an inclination surface (one end-side inclination surface 15) is provided on an opposite side of a side where the other end-side protruded part 12 is placed. Similarly, in the other end-side protruded part 12, an inclination surface (other end-side inclination surface 16) is provided on an opposite side of a side where the one end-side protruded part 11 is placed.

The base 1 includes a cylindrical wall 17 that has a cylindrical shape as a whole on an opposite side of the partition wall 6 and the blood receiving unit 8 described above (see FIG. 3(a)). An inner peripheral surface of the cylindrical wall 17 has a shape in which a bottom surface side has a small diameter and a top surface side has a large diameter with a part having an increasing diameter therebetween. Then, an inner space of the cylindrical wall 17 is connected to the communication opening 10 on the bottom surface side. Note that a whole inner space of the cylindrical wall 17 will be referred to as an air chamber 18 in the present embodiment.

A diaphragm 19 that closes the air chamber 18 is provided on a top surface side of the cylindrical wall 17. The diaphragm 19 is formed, for example, of thin elastic rubber or the like. Also, on an outer side in a radial direction of the cylindrical wall 17, an annular holder 20 that is fit into and held by the cylindrical wall 17 by piercing though the cylindrical wall 17 and that sandwiches the diaphragm 19 with the cylindrical wall 17 is provided. Here, when the diaphragm 19 is pushed toward the bottom surface side, a volume of the air chamber 18 becomes small. Thus, it is possible to pressurize the air chamber 18. Also, when the diaphragm 19 is pushed toward the bottom surface side in an initial state, a volume of the air chamber 18 becomes large when pushing is released. Thus, it is possible to depressurize the air chamber 18. Note that the pressure of the air chamber 18 may be reduced by pulling of the diaphragm 19 toward the top surface side.

Then, on an inner side of the groove part 3, a shaft-like member 21 is housed between the one end-side protruded part 11 and the other end-side protruded part 12. An outer diameter of the shaft-like member 21 is substantially the same as or a slightly smaller than an inner diameter of the measurement flow channel 4, and an entire length of the shaft-like member 21 is substantially the same as or slightly shorter than a distance between the one end-side protruded part 11 and the other end-side protruded part 12. Thus, the shaft-like member 21 is hardly moved in the groove part 3. Then, as illustrated in a partially-enlarged view in FIG. 3(*b*), a helical groove part 22 winding in a helical manner is provided in a surface of the shaft-like member 21. With this arrangement, a helical flow channel 23 is formed between wall surfaces of the groove part 3 and the blocking plate 2 and an outer peripheral surface of the shaft-like member 21. Here, the shaft-like member 21 of the present embodiment is formed by utilization of a male screw (such as male screw of M1). Thus, the shaft-like member 21 can be formed inexpensively.

Incidentally, in the measurement flow channel 4 including the helical flow channel 23, a clotting accelerator to accelerate clotting of blood is applied on the wall surface of the groove part 3 that defines these flow channels. Note that the clotting accelerator may be applied on the wall surface of the blocking plate 2 that faces the measurement flow channel 4, or the outer peripheral surface of the shaft-like member 21.

Figure 1:
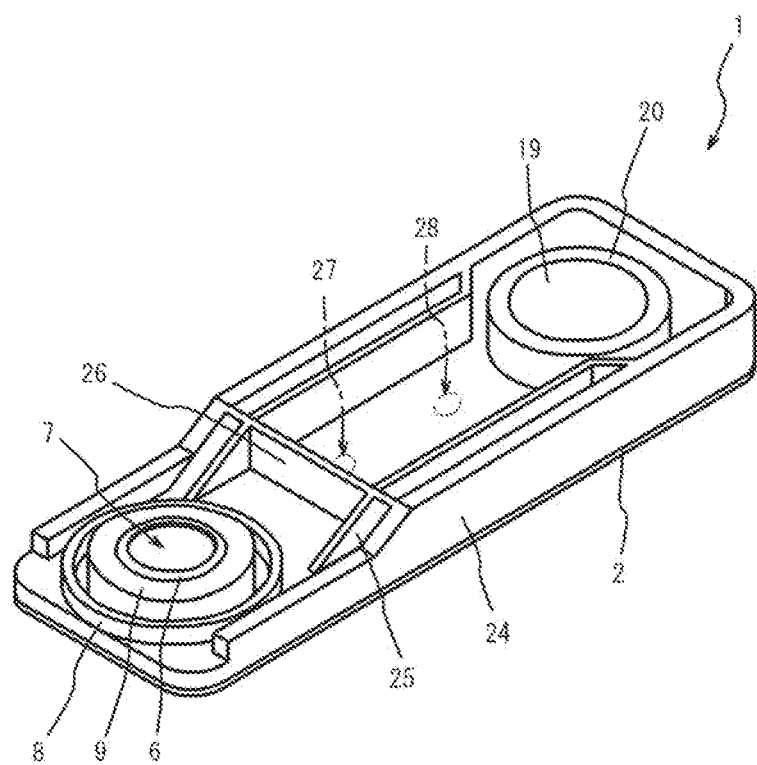
FIG. 1 is a perspective view illustrating an embodiment of a blood clotting time measurement cartridge according to the present invention.

Also, as illustrated in FIG. 1 and FIG. 2, an outer edge wall 24 that is placed in an outer edge part of the base 1 and that substantially forms a U shape in a planar view around the holder 20 is provided on a top surface of the base 1. Also, a pair of inner side walls 25 is provided on an inner side in a width direction of the outer edge wall 24. Moreover, a plate-like part (shielding part) 26 that connects the pair of inner side walls 25 is provided between the blood receiving unit 8 and the holder 20.

Also, the base 1 and the blocking plate 2 have a detection area through which light can be transmitted with respect to a predetermined part in the measurement flow channel 4. In the present embodiment, as illustrated in FIG. 3(*a*), a one end-side detection area 27 that is placed on a side of the introduction opening 5 in a vicinity of the one end-side protruded part 11, and an other end-side detection area 28 that is placed on a side of the communication opening 10 in a vicinity of the other end-side protruded part 12 are included. Note that the one end-side detection area 27 is placed on a side of the other end-side detection area 28 with respect to a shielding part 26.

The cartridge of the present embodiment in such a configuration can be set in a blood clotting time measuring device (hereinafter, referred to as "measuring device") (not illustrated) and can measure clotting time of blood. More specifically, a side on which the diaphragm 19 is placed of the cartridge extended long is inserted into the measuring device, whereby the cartridge is set in the measuring device. Note that the partition wall 6 is placed on an outer side of the measuring device in this state. Also, as illustrated in FIG. 3(*a*), a pressing means S1 that can push the diaphragm 19 for a predetermined moving amount, and a detection means that can detect existence/non-existence of blood with light are provided in the measuring device. In the detection means in the present embodiment, a one end-side light source S2 and a one end-side light receiving sensor S3 provided in such a manner as to sandwich the measurement flow channel 4 are included in the one end-side detection area 27, and an other end-side light source S4 and an other end-side light receiving sensor S5 are included in the other end-side detection area 28. Here, the one end-side light source S2 and the other end-side light source S4 emit an infrared ray, and the one end-side light receiving sensor S3 and the other end-side light receiving sensor S5 receive the emitted infrared ray. Here, in the one end-side light receiving sensor S3 and the other end-side light receiving sensor S5 of the present embodiment, a threshold is optimized in such a manner that existence/non-existence of blood can be detected according to a transmission degree of the emitted infrared ray. Note that positions of the one end-side light source S2, the one end-side light receiving sensor S3, the other end-side light source S4, and the other end-side light receiving sensor S5 may be reversed from the illustrated example, and a one end-side light source S2 and an other end-side light source S4 may be provided on a bottom surface side of a cartridge, and a one end-side light receiving sensor S3 and an other-end side light receiving sensor S5 may be provided on a top surface side of the cartridge. Also, a reflection-type sensor may be used instead of such a transmission-type sensor.

Figure 4:
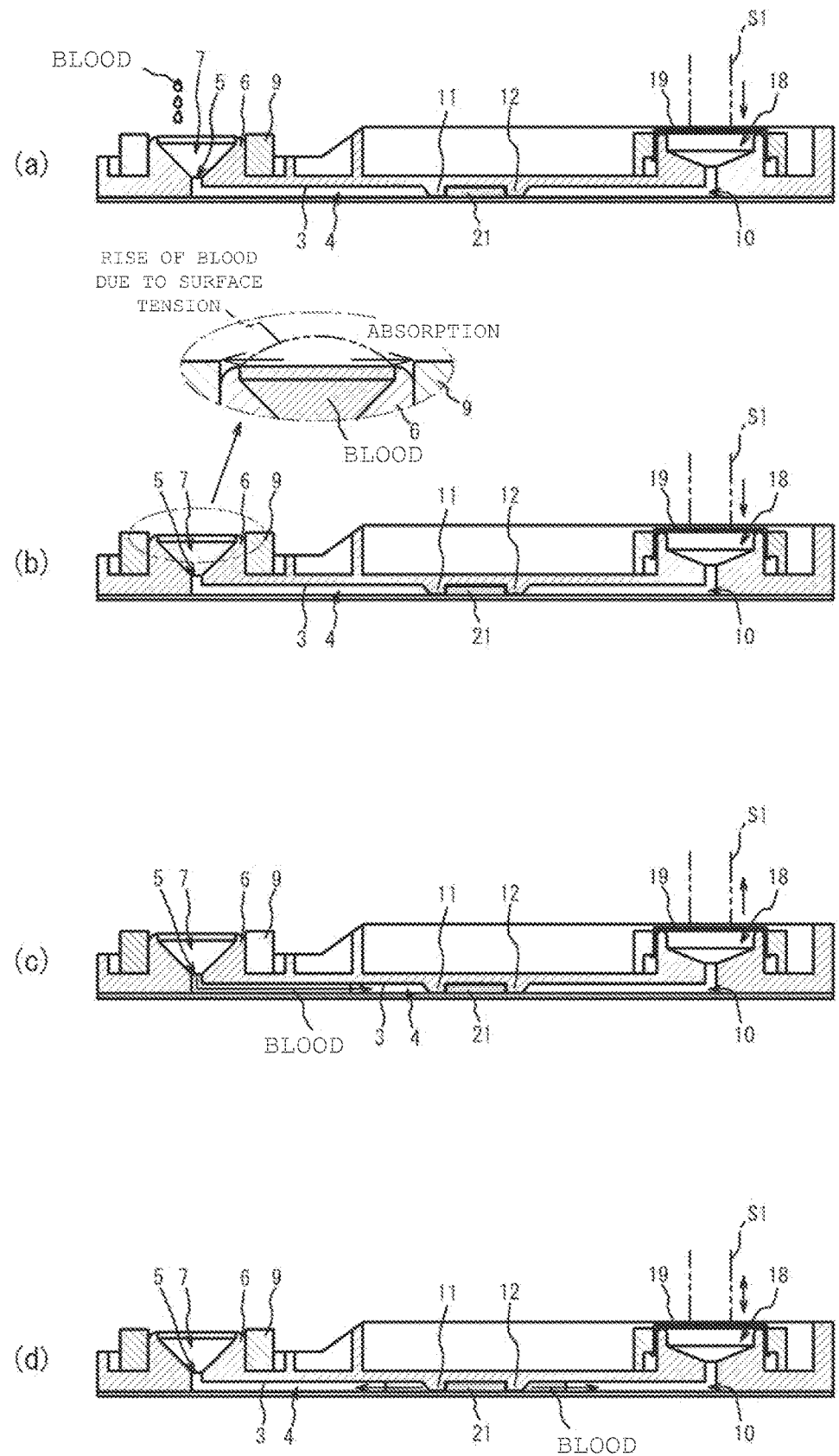
FIG. 4 is a view for describing how to use the blood clotting time measurement cartridge illustrated in FIG. 1.

Then, after the cartridge is set in the measuring device, blood to be measured is injected into the blood injection space 7 partitioned inside the partition wall 6 with a dispensing burette or the like, as illustrated in FIG. 4(*a*). Note that it is assumed that the diaphragm 19 is pushed previously by the pressing means S1 and a volume of the air chamber 18 is reduced in injection of the blood. Also, an amount of the blood injected into the blood injection space 7 is made larger than the volume of the blood injection space 7 in such a manner that the blood overflows from the partition wall 6.

Here, the blood that is beyond the upper end part of the partition wall 6 is absorbed by the absorption member 9 provided on an outer side of the partition wall 6, as illustrated in FIG. 4(*b*). In this state, the absorption member 9 absorbs blood including a portion that rises higher than the upper end part of the partition wall 6 due to surface tension in a case where the absorption member 9 is not provided. That is, after the absorption by the absorption member 9, the blood accumulates in the blood injection space 7 in such a manner as to be leveled at the height of the upper end part of the partition wall 6. Thus, an amount of the blood housed in the blood injection space 7 becomes constant. Note that as illustrated in FIG. 3(*a*), since the blood receiving unit 8 and the shielding part 26 are provided on the outer side of the absorption member 9, the blood does not flow into the one end-side detection area 27 and the other end-side detection area 28 even when an extra amount thereof is injected.

Subsequently, as illustrated in FIG. 4(*c*), the air chamber 18 is depressurized when the pushed pressing means S1 is pulled back. Thus, it is possible to suction the air in the measurement flow channel 4 from the communication opening 10, and to draw a constant amount of the blood, which is housed in the blood injection space 7, into the measurement flow channel 4. Note that in this state, the blood is drawn beyond the other end-side narrowed part 14 through the helical flow channel 23 illustrated in FIG. 3(b). It is possible to determine whether the blood is drawn beyond the other end-side narrowed part 14 on the basis of whether the blood is detected by the other end-side light receiving sensor S5. Note that since there is a correlation between a pulled amount of the pressing means S1 and an amount of the drawn blood, determination may be made on the basis of the pulled amount of the pressing means S1. Also, with a time point at which the blood is detected by the one end-side light receiving sensor S3 as a reference of the pulled amount of the pressing means S1, the blood may be drawn beyond the other end-side narrowed part 14 on the basis of a pulled amount therefrom.

Subsequently, the pressing means S1 is pushed again and the air chamber 18 is pressurized, whereby the blood in the measurement flow channel 4 is moved toward the one end-side narrowed part 13. Accordingly, it is possible to oppositely move the blood passing through the helical flow channel 23 toward the other end-side narrowed part 14.

Since it is possible to pressurize or to depressurize the air chamber 18 by repeating pushing and pulling of the pressing means S1 in such a manner, the air or the blood in the measurement flow channel 4 is pressurized or suctioned through the communication opening 10, and it is possible to make the blood make a reciprocating motion in association therewith (see FIG. 4(d)). That is, since a direction of a flow is switched, the blood can be stirred. Also, since a speed of a flow and the like change when the blood passes through the one end-side narrowed part 13 or the other end-side narrowed part 14, stirring is also performed efficiently in this point. Moreover, since the blood is made to pass through the helical flow channel 23, stirring thereof can be performed more efficiently in the present embodiment. By the stirring of the blood in such a manner, it is possible to efficiently and stably dissolve the clotting accelerator applied on the wall surface of the groove part 3, or the like into the blood.

Then, when the blood is stirred and the clotting accelerator is dissolved, viscosity of the blood is increased, and a flow of the blood becomes deteriorated in the one end-side narrowed part 13, the other end-side narrowed part 14, the helical flow channel 23, or the like. That is, since a cycle of a reciprocating motion of the blood detected by the one end-side light receiving sensor S3 and the other end-side light receiving sensor S5 in a state in which the blood is not clotted, and a cycle of a reciprocating motion detected by the one end-side light receiving sensor S3 and the like when a flow of the blood is deteriorated are different even when timing of pushing or pulling the pressing means S1 is not changed, it is possible to calculate clotting time of the blood on the basis of this change in time necessary for the reciprocating motion. Note that since the amount of the blood introduced into the measurement flow channel 4 is constant, a ratio of the previously-applied clotting accelerator to the introduced blood does not change regardless of viscosity of the introduced blood, or the like. Thus, clotting time of the blood can be accurately measured.

Note that when a speed of a flow or the like changes suddenly when the blood passes through the one end-side narrowed part 13 or the other end-side narrowed part 14, there is a case where the air in the measurement flow channel 4 is involved and an air bubble is generated, and there is a possibility that this bubble affects detection of the blood in the one end-side light receiving sensor S3 and the other end-side light receiving sensor S5. On the one hand, in the present embodiment, a speed of a flow or the like is made to change gradually by provision of the one end-side inclination surface 15 and the other end-side inclination surface 16. Thus, the air bubble is less likely to be generated, and accuracy in detection of existence/non-existence of the blood can be more stabilized.

In the above, a cartridge and a measuring device according to the present invention have been described with a specific embodiment. However, the cartridge according to the present invention is not limited to the above-described embodiment, and various modifications are made within the scope of the claims. For example, the helical flow channel 23 in the present embodiment includes the groove part 3 provided in the base 1, and the shaft-like member 21 housed in this groove part 3. However, what includes a helical groove in a base 1 may be used. Also, various methods can be employed as a method of fixing a diaphragm 19. For example, fixation to a base 1 may be performed by utilization of an adhesive or the like. Also, a detection area may be provided on any one of one end side and the other end side, or may be provided in three or more places. Moreover, as illustrated in FIG. 2, in the present embodiment, the one end-side detection area 27 is provided between the introduction opening 5 and the shaft-like member 21, and the other end-side detection area 28 is provided between the communication opening 10 and the shaft-like member 21. However, both detection areas may be provided between an introduction opening 5 and a shaft-like member 21, or may be provided between a communication opening 10 and a shaft-like member 21.

Also, an absorption member 9 may have a thickness with which an upper end part thereof becomes lower than an upper end part of a partition wall 6 and may have a shape of being provided in a part of a whole circumference of the partition wall 6 which shape is, for example, a semicircle shape, but preferably has a thickness with which an upper end part of the absorption member 9 is placed as high as or higher than an upper end part of a partition wall 6 and has a shape of surrounding a whole circumference of the partition wall 6 in a manner described above from a point that blood that is beyond the upper end part of the partition wall 6 can be stably absorbed. Also, a shape of an absorption member 9 is not limited to an annular shape, and can be variously modified, for example, to a shape in which an inner peripheral surface is a circular hole and an outer peripheral surface has a polygonal shape (such as square shape or hexagonal shape). Also, in the illustrated absorption member 9, an inner peripheral surface thereof is in contact with the outer peripheral surface of the partition wall 6 without a gap. However, there may be a gap for a certain degree (such as about 1 mm).

REFERENCE SIGNS LIST 1 base
2 blocking plate
3 groove part
4 measurement flow channel
5 introduction opening
6 partition wall
7 blood injection space
8 blood receiving unit
9 absorption member
10 communication opening
11 one end-side protruded part
12 other end-side protruded part
13 one end-side narrowed part 14 other end-side narrowed part
15 one end-side inclination surface
16 other end-side inclination surface
17 cylindrical wall
18 air chamber
19 diaphragm
20 holder
21 shaft-like member
22 helical groove part
23 helical flow channel
24 outer edge wall
25 inner side wall
26 shielding part
27 one end-side detection area
28 other end-side detection area

The invention claimed is:

1. A blood clotting time measurement cartridge comprising:
   a measurement flow channel in which blood is housed and it is detected whether there is blood in a predetermined position by transmission of light;
   an introduction opening which is provided on one end side of the measurement flow channel and from which blood is introduced into the measurement flow channel;
   a communication opening which is provided on the other end side of the measurement flow channel and through which it is possible to cause, by suction or pressurization of air in the measurement flow channel or the blood introduced from the introduction opening into the measurement flow channel, the blood in the measurement flow channel to make a reciprocating motion in such a manner as to pass through the predetermined position;
   a partition wall to partition a blood injection space connected to the introduction opening; and
   an absorption member that has an annular shape and fits on an outer peripheral surface of the partition wall in a manner extending from a base portion of the outer peripheral wall to a position whereby an upper end part of the absorption member is placed as high as or higher than an upper end part of the partition wall; and
   wherein the absorption member absorbs blood that is beyond the partition wall when a larger amount of blood than the volume of the blood injection space is injected into the blood injection space.

2. The blood clotting time measurement cartridge according to claim 1, wherein the absorption member surrounds a whole circumference of the partition wall.

3. A blood clotting time measuring device to which the blood clotting time measurement cartridge according to claim 1 is attached, the device comprising a detector that detects with light whether there is blood in the predetermined position.

4. A blood clotting time measuring device to which the blood clotting time measurement cartridge according to claim 2 is attached, the device comprising a detector that detects with light whether there is blood in the predetermined position.

* * * * *